US00PP35745P3

(12) United States Plant Patent
Valin

(10) Patent No.: US PP35,745 P3
(45) Date of Patent: Apr. 16, 2024

(54) ROSE PLANT NAMED 'TMRO14-02'

(50) Latin Name: ***Rosa* x *hybrida***
Varietal Denomination: TMRO14-02

(71) Applicant: Branded Garden Products Ltd., Ipswich (GB)

(72) Inventor: Charles Valin, Ipswich (GB)

( * ) Notice: Subject to any disclaimer, the term of this patent is extended or adjusted under 35 U.S.C. 154(b) by 0 days.

(21) Appl. No.: 18/186,168

(22) Filed: Mar. 19, 2023

(65) Prior Publication Data

US 2023/0329129 P1 Oct. 12, 2023

Related U.S. Application Data

(60) Provisional application No. 63/330,069, filed on Apr. 12, 2022.

(51) Int. Cl.
*A01H 5/02* (2018.01)
*A01H 6/74* (2018.01)

(52) U.S. Cl.
USPC ..... Plt./101
CPC ..... *A01H 6/749* (2018.05)

(58) Field of Classification Search
USPC ..... Plt./101
CPC ..... A01H 6/749; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new cultivar of *Rosa* named 'TMRO14-02' that is distinguishable by a semi-prostrate plant habit with pendulous branches when grown in hanging containers, mid-sized glossy green leaves, double self-cleaning fragrant flowers which open and remain lemon yellow in color until the flowers age to white. 'TMRO14-02' exhibits high disease resistance and is hardy to USDA Zone 5. In combination these traits set 'TMRO14-02' apart from all other existing varieties of *Rosa* known to the inventor.

2 Drawing Sheets

Genus and species: *Rosa* x *hybrida*.
Variety denomination: 'TMRO14-02'.

BACKGROUND

The present invention comprises a new and distinct variety of rose, botanically known as *Rosa* x *hybrida* and hereinafter referred to by the variety name 'TMRO14-02'. The new variety of rose plant originated from a controlled crossing in Ipswich, United Kingdom in 2011. The crossing was between the proprietary female rose variety 'Sweet Fairy' (unpatented) and the proprietary male rose variety 'Immensee' (unpatented). The resulting seeds were planted and the resulting seedlings were evaluated. The new rose plant was selected in 2014 in Ipswich, United Kingdom and named 'TMRO14-02'. 'TMRO14-02' was found to reproduce true to type in successive generations of asexual propagation carried out by the inventor in Ipswich, United Kingdom using the method of vegetative cuttings.

SUMMARY

The following are the most outstanding and distinguishing characteristics of the new variety 'TMRO14-02' when grown under normal horticultural practices.

1. 'TMRO14-02' exhibits a semi-prostrate plant habit with pendulous branches when grown in containers.
2. 'TMRO14-02' bears mid-sized glossy green leaves.
3. 'TMRO14-02' bears double flowers which open and remain lemon yellow in color for 20-25 days until first petals fall.
4. The flowers of 'TMRO14-02' become white with age.
5. The flowers of 'TMRO14-02' are self-cleaning.

6. The flowers of 'TMRO14-02' are barren: no seed has been observed.
7. The flowers of 'TMRO14-02' are pleasantly and characteristically rose fragrant.
8. 'TMRO14-02' exhibits high disease resistance.
9. 'TMRO14-02' is hardy in USDA Hardiness Zone 5.

These traits in combination distinguish 'TMRO14-02' from all other existing varieties of *Rosa* known to the inventor. 'TMRO14-02' has not been tested under all possible conditions and phenotypic differences may be observed with variations in environmental, climatic, and cultural conditions, without any variance in genotype.

DESCRIPTION OF THE PHOTOGRAPHS

The accompanying photographs show, as nearly true as it is reasonably possible to make in color illustrations of this type, typical flower and foliage characteristics of the new cultivar. Colors in the photographs may differ slightly from the color values cited in the detailed description, which accurately describes the colors of 'TMRO14-02'.

Both drawings were made using conventional techniques and although flower and foliage color may appear different from actual color due to light reflectance, they are as accurate as possible by conventional photography.

DESCRIPTION OF THE NEW VARIETY

Figure 1:
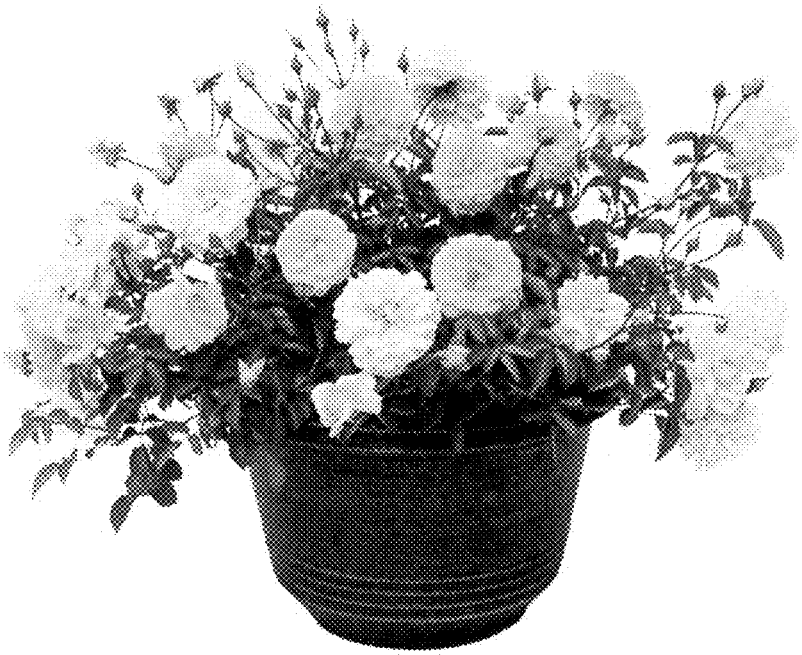
FIG. 1 illustrates the overall growth and flowering habit of 'TMRO14-02' at 12 months old growing out of doors in Santa Barbara, California in a 20 cm diameter container.
Figure 2:
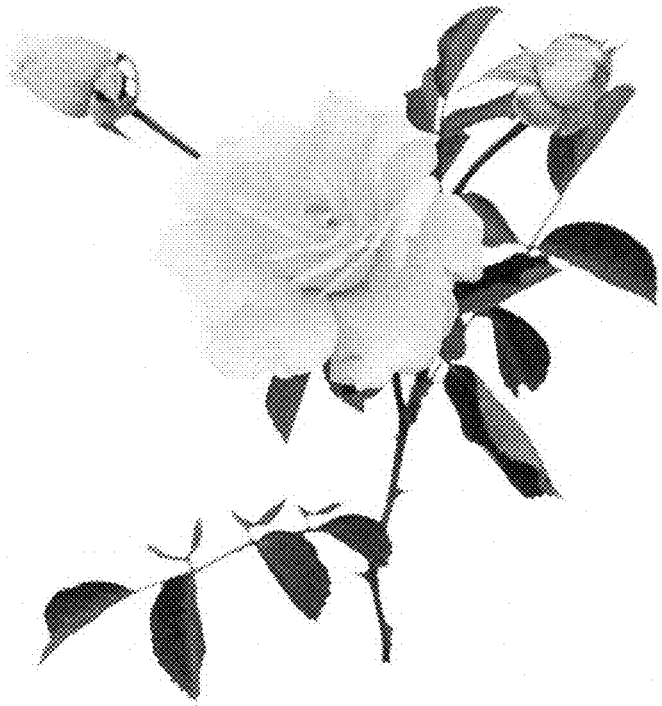
FIG. 2 illustrates a close-up view of an individual flower and buds of 'TMRO14-02'.

The following is a detailed botanical description of the new *Rosa* cultivar named 'TMRO14-02'. Observations, measurements, values and comparisons were collected in Carpinteria, California from a 12 month old plant growing in a 20 cm diameter container. Color determinations were made in accordance with The 2007 Royal Horticultural Society Colour Chart from London England, except where general color terms of ordinary dictionary significance are used. Growing requirements are similar to the species.

Botanical classification:

*Family*.—Rosaceae.

*Genus*.—*Rosa*.

*Species*.—x *hybrida*.

*Common name*.—Rose.

Parentage: *Rosa* x *hybrida* 'TMRO14-02' is a seedling that resulted from the controlled cross-pollination of the following parents:

*Female parent*.—*Rosa* variety 'Sweet Fairy' (unpatented).

*Male parent*.—*Rosa* variety 'Immensee' (unpatented).

Plant:

*Propagation method*.—Softwood cuttings.

*Rooting system*.—Fine and fibrous.

*Root color*.—NN155D aging to 164D.

*Growth type, vigor*.—Moderate, vigorous dwarf shrub rose, remaining compact.

*Habit*.—Semi-prostrate.

*Use*.—For use in the garden and landscape and suitable for planting in containers and hanging baskets.

*Type*.—Perennial.

*Plant dimensions*.—After one year's growth from a rooted cutting, plants of 'TMRO14-02' are 40 cm-45 cm in width and 12 cm-15 cm in height.

*Cultural requirements*.—Grow in full sun with regular water, and well-draining media.

*Pest and disease resistance*.—'TMRO-14-02' appears to be resistant to commonly observed diseases of roses, including to rust (phragmidium species), powdery mildew (*Podosphaera pannosa*) and blackspot (*Diplocarpon rosae*).

*Hardiness*.—USDA Zone 5.

Stem, branches: When a rooted cutting is transplanted into the growing container, the cutting is pinched or stopped above the first node, creating a short basal stem at ground level. New growth develops from the basal stem (basal branching stems). All basal branching stems develop terminal inflorescences and bear lateral compound leaves.

*Basal stem*.—Shape: Cylindrical. Dimensions: Length 1 cm, diameter 0.8 cm-1.0 cm. Color: 146D. Surface: Smooth.

*Branching stems*.—Shape: Cylindrical. Dimensions: Length 30 cm-35 cm, diameter at base 5 mm. Color: 146D with anthocyanin present on upper (newer) growth; anthocyanin coloration 59C. Surface: Smooth.

*Internode length*.—Ranges between 3 cm and 7 cm.

*Thorns*.—Description: Medium-sized thorns distributed along the entire length of the branches. Quantity: Average 35 per stem at average distance of 1 thorn per 1 cm but closer towards base. Aspect: Outward facing at right angles to stem. Shape: Deltoid with elliptic base. Length: 9 mm. Base dimensions: Length 5 mm, width 2.5 mm. Color: N34C.

Foliage:

*Description*.—Compound, consisting of 7 leaflets of which 3 leaflets arranged in opposite pairs and 1 terminal leaflet.

*Dimensions* (*overall, compound leaf*).—7 cm-9 cm in length, 5 cm-7 cm in width.

*Attachment* (*compound leaf*).—Petiolate.

*Petiole shape, dimensions*.—Cylindrical, 1.8 cm in length, 1.0 mm-1.5 mm in diameter.

*Petiole surface*.—Smooth with small thorns at leaflet base.

*Petiole color*.—146D with anthocyanin present on upper (newer) petioles; anthocyanin coloration 59C.

*Thorns*.—1.5 mm-2 mm in length, 0.5 mm in width, smooth, same color as petiole.

*Leaflets*.—Quantity: 7 leaflets (arranged as three opposite pairs and one terminal leaflet). Type: Evergreen. Shape: Obovate. Dimensions (each paired leaflet): 4 cm-5.5 cm in length, 1.5 cm-2.5 cm in width. Dimensions (terminal leaflet): 6 cm in length, 2.7 cm in width.

*Attachment*.—Petiolate (petiolules). Petiolule dimensions: 1.5 mm-1.8 mm in length, 1 mm in diameter. Petiolule surface: Smooth. Petiolule color: 146D with anthocyanin 59C present on upper (newer) petiolules.

*Color* (*adaxial surface*).—137A.

*Color* (*abaxial surface*).—138B.

*Base shape*.—Rounded, occasionally oblique.

*Apex shape*.—Acuminate.

*Texture*.—Leathery, glossy.

*Margin*.—Serrate. Teeth aspect: Pointing towards apex. Teeth quantity: 18-21 teeth per leaflet edge. Teeth depth: 0.5 mm-1.0 mm.

*Venation*.—Reticulate. Veins (adaxial surface): Faint, color 138C. Veins (abaxial surface): Midrib prominently raised, vein color 138C.

*Stipules*.—Present at compound leaf attachment to stem.

*Stipule description*.—Irregularly lanceolate, 15 mm in length, 6 mm in width; mostly fused to stem, free towards stipule apex; smooth, color 138C.

*Foliage pest and disease resistance*.—No susceptibility to pests or diseases has been observed.

Inflorescence:

*Inflorescence type*.—Terminal.

*Inflorescence quantity*.—25 (average per plant).

*Shape of inflorescence*.—Flat-topped cylindrical, upright-facing.

*Dimensions of inflorescence* (*average*).—16 cm in diameter and 5 cm in height.

*Inflorescence shape, profile*.—Radiate, basally concave.

*Blooming seasons*.—Spring through fall. Flower production is increased by removal of spent flowers.

*Bud*.—Shape: Pointed ovoid. Dimensions (immediately prior to petal color first showing): 15 mm in height and 13 mm in diameter. Color: 141C with tinges of anthocyanin 185C.

*Sepals*.—Quantity: 5, strongly recurved, abaxial surface presents outward facing. Sepal shape: Deltoid with pronounced extended (2 mm) acuminate apex. Sepal dimensions: Length (including acuminate apex) 21 mm, width 8 mm. Sepal surface (adaxial): Smooth with short fine erect hairs, hair length 0.5 mm. Sepal surface (abaxial): Heavily tomentose, hairs fine, 0.5 mm-1.0 mm in length, parallel to sepal surface. Sepal margin: markedly pubescent, hairs 1 mm-1.5 mm in length, color white NN155D and occasionally very light pink N155D.

*Receptacles*.—Shape: Funnel. Dimensions: 7 cm in length, 6 cm in diameter. Surface: Smooth. Color: 141C.

*Peduncle*.—Shape: Cylindrical. Dimensions: 4 cm in length, 1.5 mm in diameter. Color: 61A. Surface: Smooth with short erect hairs, length less than 1 mm, color 59A.

*Blooms*.—Size: 5.5 cm-6.0 cm in diameter, 2 cm in height. Borne: Singly. Fragrance: Pleasant when approached closely, typical of scented roses. Lastingness: Individual blooms last for 20-25 days on the plant, and for 10-15 days off the plant, from first petal opening to first petal fall.

*Petals*.—Arrangement: Typically, 5 petals in each of 8 closely arranged layered whorls. Number: Approximately 40 per bloom. Form: Recurved and wavy. Dimensions: 25 mm in length, 18 mm in width. Shape: Obcordate, base acute, apex depressed (concave), rounded. Apex: Round. Base: Truncate. No petal base spot. Texture: Delicate, translucent towards margins. Margins: Smooth, entire. Color (both surfaces, bloom freshly open): 14B towards petal base, 13C towards petal apex. Color (both surfaces, bloom aged and petals about to drop): NN155C.

*Petaloids*.—Description: Multiple petaloids (8-10 in number) arising around and from within the reproductive organs. Shape: Irregularly elliptic, length 5 mm-8 mm, width 3 mm-4 mm. Color: 13C.

Reproductive organs:

*Stamens*.—Number: 50-55. Arrangement: Radiating around bundle of pistils. Filaments 6 mm-7 mm in length, less than 0.5 mm in diameter. Filament color: 12B.

*Anthers*.—Shape, dimensions: Truncated ellipsoid, length 2 mm, width 1.5 mm. Attachment: Fragile, readily shed when touched. Color (freshly opened blooms): 17B. Color (senescent blooms): Near black, 202A.

*Pollen*.—None observed.

*Pistil*.—Styles: Number: 15-20. Arrangement: Free, closely packed bundle. Dimensions: 4 mm in length, less than 0.25 mm in diameter. Color: 64C.

*Stigmas*.—Dimensions: 1 mm in length, less than 0.25 mm in diameter. Color: 12B.

*Ovaries*.—Appear rudimentary or undeveloped.

Fruit (hips) or seed: None observed. Flowers are barren, pollination has not occurred.

COMPARISON WITH COMMERCIAL LINES

'TMRO14-12' can be compared to the commercial variety 'Flower Carpet Sunshine' (unpatented). Differences between the two varieties are described in Table 1:

TABLE 1

Comparison with Similar Variety

| Characteristic | 'TMRO14-12' | 'Flower Carpet Sunshine' |
|---|---|---|
| Habit | Trailing | Compact arching and trailing habit |
| Flowers | Double lemon yellow flowers | Soft lemon yellow flowers |

'TMRO14-12' can be compared to the commercial variety 'Flower Carpet White' (U.S. Plant Pat. No. 9,573). Differences between the two varieties are described in Table 2:

TABLE 2

Comparison with Similar Variety

| Characteristic | 'TMRO14-12' | 'Flower Carpet White' |
|---|---|---|
| Habit | Trailing | Compact arching and trailing habit |
| Flowers | Double lemon yellow flowers | Soft lemon yellow flowers |

COMPARISON WITH PARENTS

'TMRO14-12' can be compared to the female parent variety 'Sweet Fairy'. Differences between the two varieties are described in Table 3:

TABLE 3

Comparison with Female Parent Variety

| Characteristic | 'TMRO14-12' | 'Sweet Fairy' |
|---|---|---|
| Commercial type | Shrub Rose | Miniature Rose |
| Flower color | Lemon yellow | White, blushed light pink |
| Flower form | Double | Single |

'TMRO14-12' can be compared to the male parent variety 'Immensee' Differences between the two varieties are described in Table 4:

TABLE 4

Comparison with Male Parent Variety

| Characteristic | 'TMRO14-12' | 'Immensee' |
|---|---|---|
| Habit | Semi-prostrate | Prostrate, ground cover |
| Flower color | Lemon yellow | Pink |

I claim:

1. A new and distinct cultivar of *Rosa* Plant Named 'TMRO14-02' as described and illustrated herein.

* * * * *